(12) United States Patent
Marino et al.

(10) Patent No.: US 8,021,400 B2
(45) Date of Patent: Sep. 20, 2011

(54) SPINAL TRANSVERSE CONNECTOR

(75) Inventors: James F. Marino, La Jolla, CA (US); Jamil Elbanna, San Diego, CA (US)

(73) Assignee: Trinity Orthopedics LLC, San Diego, CA (US)

( * ) Notice: Subject to any disclaimer, the term of this patent is extended or adjusted under 35 U.S.C. 154(b) by 304 days.

(21) Appl. No.: 12/326,768

(22) Filed: Dec. 2, 2008

(65) Prior Publication Data

US 2009/0157120 A1    Jun. 18, 2009

Related U.S. Application Data

(60) Provisional application No. 61/013,595, filed on Dec. 13, 2007.

(51) Int. Cl.
*A61B 17/70* (2006.01)

(52) U.S. Cl. .................. 606/278; 606/250; 606/260

(58) Field of Classification Search .......... 606/250–253, 606/260, 278, 60, 61, 246–248, 257–259, 606/261
See application file for complete search history.

(56) References Cited

U.S. PATENT DOCUMENTS

| | | |
|---|---|---|
| 5,275,600 A | 1/1994 | Allard et al. |
| 5,330,473 A * | 7/1994 | Howland .................. 606/250 |
| 5,474,555 A | 12/1995 | Puno et al. |
| 5,498,262 A | 3/1996 | Bryan |
| 5,549,607 A | 8/1996 | Olson et al. |
| 5,601,554 A | 2/1997 | Howland et al. |
| 5,624,442 A | 4/1997 | Mellinger et al. |
| 5,947,966 A | 9/1999 | Drewry |
| 6,110,173 A | 8/2000 | Thomas, Jr. |
| 6,136,003 A | 10/2000 | Hoeck et al. |
| 6,217,578 B1 | 4/2001 | Crozet et al. |
| 6,283,967 B1 | 9/2001 | Troxell et al. |
| 6,306,137 B2 | 10/2001 | Troxell |

(Continued)

FOREIGN PATENT DOCUMENTS

WO    00/59387    10/2000

(Continued)

OTHER PUBLICATIONS

Expedium SFX Cross Connector; DePuy Spine Product literature (http://www.onlinespinecenter.com/tabid/159/Default.aspx?id=520), 2009.

(Continued)

*Primary Examiner* — Eduardo C Robert
*Assistant Examiner* — Christina Negrelli
(74) *Attorney, Agent, or Firm* — Fred C. Hernandez; Mintz, Levin, Cohn, Ferris, Glovsky and Popeo, P.C.

(57) ABSTRACT

Disclosed is a spinal transconnector device for coupling longitudinal spinal rods on either side of the mid-sagittal plane. The device includes two interconnected rod engagement elements, a first rod engagement elements having a vaulted surface adapted to secure to a first longitudinal spinal rod via an interference fit comprising compression of the first longitudinal spinal rod against the generally vaulted surface; and an interference pin that advances into a bore of the first rod engagement element forming an interference fit between the interference pin and the rod engagement element. The interference fit can be associated with elastic deformation of the first rod engagement element occurring as a consequence of the interference pin being advanced through the bore in the engagement element and contacting a surface of the first longitudinal spinal rod.

8 Claims, 6 Drawing Sheets

U.S. PATENT DOCUMENTS

| | | |
|---|---|---|
| 6,554,831 B1 | 4/2003 | Rivard |
| 6,554,832 B2 | 4/2003 | Shluzas |
| 6,616,668 B2 | 9/2003 | Altarac et al. |
| 6,761,721 B2 | 7/2004 | Burgess et al. |
| 6,802,844 B2 | 10/2004 | Ferree |
| 6,872,208 B1 | 3/2005 | McBride et al. |
| 6,887,241 B1 | 5/2005 | McBride |
| 6,986,771 B2 | 1/2006 | Paul et al. |
| 6,989,011 B2 | 1/2006 | Paul et al. |
| 7,083,622 B2 | 8/2006 | Simonson |
| 7,104,993 B2 | 9/2006 | Baynham et al. |
| 7,137,986 B2 | 11/2006 | Troxell et al. |
| 7,207,992 B2 | 4/2007 | Ritland |
| 7,220,262 B1 | 5/2007 | Hynes |
| 2002/0143330 A1* | 10/2002 | Shluzas .................... 606/61 |
| 2003/0114853 A1 | 6/2003 | Burgess et al. |
| 2004/0116928 A1 | 6/2004 | Young et al. |
| 2004/0133203 A1 | 7/2004 | Young et al. |
| 2005/0107789 A1 | 5/2005 | Sweeney |
| 2005/0113927 A1 | 5/2005 | Malek |
| 2005/0228376 A1 | 10/2005 | Boomer et al. |
| 2005/0228377 A1 | 10/2005 | Chao |
| 2006/0041259 A1 | 2/2006 | Paul et al. |
| 2006/0064093 A1 | 3/2006 | Thramann et al. |
| 2006/0217712 A1 | 9/2006 | Mueller et al. |
| 2006/0241598 A1 | 10/2006 | Khalili |
| 2006/0247779 A1 | 11/2006 | Gordon et al. |
| 2006/0271045 A1 | 11/2006 | Hubbard et al. |
| 2007/0073289 A1 | 3/2007 | Kwak et al. |
| 2007/0185492 A1 | 8/2007 | Chervitz et al. |
| 2008/0234759 A1 | 9/2008 | Marino |

FOREIGN PATENT DOCUMENTS

| | | |
|---|---|---|
| WO | WO2009076107 | 6/2009 |

OTHER PUBLICATIONS

Crossover System; DePuy Spine Product literature (http://onlinespinecenter.com/tabid/159/Default.aspx?id=262), 2009.

Universal Spine System; Synthes North America Product literature (http://us.synthes.com/Products/Spine/Deformity/Universal+Spine+System.htm), 2009.

X10 Crosslink; Medtronic Sofamor Danek Product literature (http://www.sofamordanek.com/patient-x10crosslink.html), 2007.

\* cited by examiner

SPINAL TRANSVERSE CONNECTOR

REFERENCE TO PRIORITY DOCUMENT

This application claims the benefit of priority of co-pending U.S. provisional patent application Ser. No. 61/013,595, entitled "Spinal Transverse Connector," filed Dec. 13, 2007. Priority of the aforementioned filing date is hereby claimed and the entire disclosure of which is hereby incorporated by reference.

BACKGROUND

The use of spinal rods is conventional for correction of spinal trauma or conditions, such as curvature of the spine. Generally, an orthopedic stabilization system may include a pair of spinal rods that are coupled to a bone or bones. The rods are generally contoured and longitudinally disposed adjacent to vertebral bodies of a spine.

In some cases, a pair of spinal rods are fastened in parallel on either side of the spinous process. The assembly can be significantly strengthened by using at least one additional stiffening member known as a transverse connector or cross link to horizontally connect the pair of spine rods. A number of different transverse connectors are known. Generally, the transverse connectors should provide strength and control torsion. Stresses can act to return a stabilized bone system to a deformed position. For example, stresses on a spine and on a spinal stabilization system often operate to return a corrected spine to a deformed position. Transverse connectors can inhibit rod movement of the spinal stabilization system during a post-operative period so that the spine remains in a corrected position.

Rods of an orthopedic stabilization system can be aligned along a longitudinal axis of the spine generally parallel to each other on each side of the midline of the spine. Due to a wide variety of factors, two rods are rarely three dimensionally geometrically aligned. That is, two rods very rarely are located a uniform distance from each other along their entire length. Generally, the two rods have some convergence or divergence in the medial-lateral direction. The two rods may also not have the same orientation with respect to the coronal plane. The rods might also not have a coplanar geometry from a lateral view.

To address the variations of geometrical alignment, surgeons sometimes will bend the rods to accommodate a transverse connector or bend the transverse connector to accommodate the rods. In addition, transverse connectors have been developed that have some adjustability to adapt for variations from geometrical alignment. Two piece transverse connectors allow for the stabilization of rods that are oriented in different horizontal and vertical planes. Further, the connection between multi-shaft transverse connectors must resist shear to avoid separation and provide stability to the rods.

Because of the forces acting along the transverse connector and the movement of the spinal rods, the connection between the transverse connector and the rod must be secure to avoid movement of the transverse connector along the spinal rod. Some rod fastening systems of transverse connectors use threaded fasteners to attach the transverse connector to adjacent rods. The threaded fastener can be a set screw or a nut. Not tightening a threaded fastener enough may allow movement of the transverse connector. Overtightening a threaded fastener could result in damage to the system and failure of the transverse connector.

Installation of a spinal fixation device is a lengthy and complicated surgical procedure. Simplification of the assembly of the device will tend to reduce the complications associated with the procedure.

SUMMARY

There is a growing need for improved devices that link tissue structures in an animal body. In particular, there is a need for a simple spine fixation assembly having a minimum of components and a minimum of steps for installation. Further, there is a need for an easily adjustable transverse connector that can accommodate a variety of geometrical orientations. There is also a need for a transverse connector that resists movement along the spinal rod and a connector that avoids contact with the dura and spinal column during installation.

Disclosed in the present application is an apparatus that includes a central universal joint element that maintains the transverse connector in an A-frame architecture to protect the dura of the spinal column. The axis of the joint element of the device is roughly parallel with the general axis of the connecting rod elements.

In one embodiment, disclosed is a spinal transconnector device for coupling longitudinal spinal rods on either side of the mid-sagittal plane. The device includes two interconnected rod engagement elements, a first rod engagement element having a vaulted surface adapted to secure to a first longitudinal spinal rod via an interference fit comprising compression of the first longitudinal spinal rod against the generally vaulted surface. The device also includes an interference pin that advances into a bore of the first rod engagement element forming an interference fit between the interference pin and the rod engagement element. The interference fit is associated with elastic deformation of the first rod engagement element occurring as a consequence of the interference pin being advanced through the bore in the engagement element and contacting a surface of the first longitudinal spinal rod.

In another embodiment, disclosed is a spinal transconnector device for coupling longitudinal spinal rods on either side of the mid-sagittal plane that includes a first rod engagement element having a convex spherical element and a second rod engagement element. The second rod engagement element has a passage for receiving the convex spherical element, at least a portion of the passage having a first concave spherical surface geometry that can mate with at least a portion of the convex spherical element and an interference element having a second concave spherical surface geometry. The convex spherical element articulates within the passage and is sandwiched between the first concave spherical surface of the passage and the second concave spherical surface of the interference element.

In another embodiment, disclosed is a spinal transconnector device for coupling longitudinal spinal rods on either side of the mid-sagittal plane that includes two interconnected rod engagement elements each adapted to secure to a respective longitudinal spinal rod, the rod engagement elements interconnected in a manner that permits relative articulation therebetween. The relative articulation of the two rod engagement elements results from the separation or approximation of contacting elements of a deployment tool that engage surfaces on either of the rod engagement elements. Each contacting element has a mating surface with a generally spherical geometry.

In another embodiment, disclosed is a spinal transconnector device for coupling longitudinal spinal rods on either side of the mid-sagiftal plane that includes two interconnected rod engagement elements that are coupled by mating surfaces with segments of generally spherical surfaces, the rod engagement elements connected in a male-female relationship through an aperture, wherein the diameter of either of the mating spherical surfaces exceeds the diameter of the aperture.

In another embodiment, disclosed is a spinal transverse connector device for coupling spinal rods including first and second longitudinal elements, a connector element, and first and second interference elements. The first longitudinal element includes a threaded bore and a passage having a portion that intersects a portion of the threaded bore. The second longitudinal element includes a bore. The connector element connects the first and second longitudinal elements and includes a convex spherical region and a stem region. The convex spherical region extends into the passage of the first longitudinal element and the stem region extends into the bore of the second longitudinal element. The convex spherical region has a diameter that exceeds a diameter of an opening into the passage. The opening into the passage is surrounded by internal walls having partially spherical concave surface geometry. The first interference element includes a first surface that has a generally concave conical geometry and a second surface that has a generally concave spherical geometry. The second interference element includes a first region that has a convex truncated conical surface geometry and a second region that has a threaded surface geometry. Advancement of the second interference element into the threaded bore presses the first region of the second interference element against the first surface of the first interference element displacing the first interference element towards the convex spherical region of the connector element thereby pressing the convex spherical region against the internal walls surrounding the passage opening therein forming three generally spherical mating surfaces whose approximation to each other inhibits relative movement between the first and second longitudinal elements.

Other features and advantages will be apparent from the following description of various embodiments, which illustrate, by way of example, the principles of the disclosed devices and methods.

DETAILED DESCRIPTION

Figure 1:
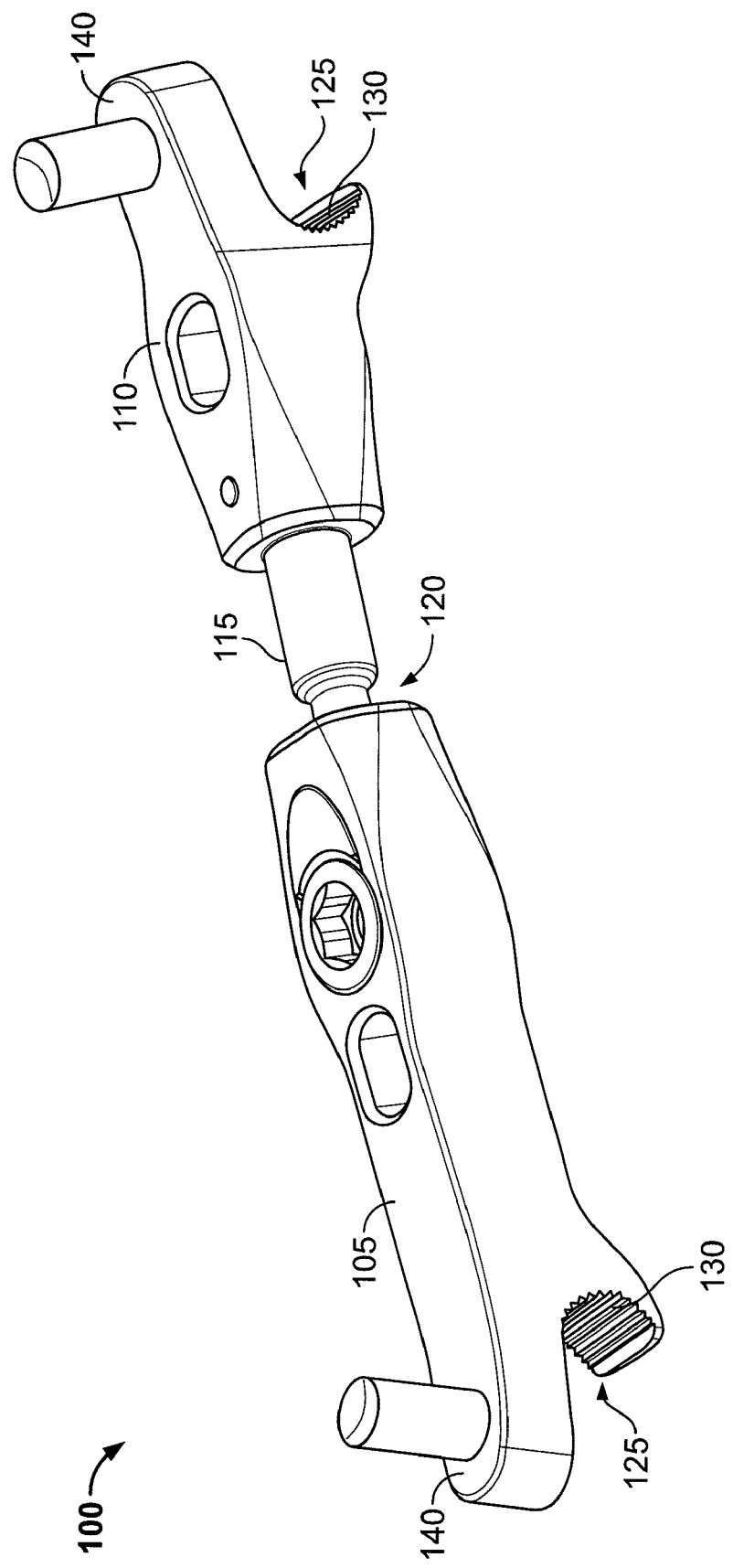
FIG. 1 shows a perspective view of one embodiment of a transverse connector assembly.

FIG. 1 shows an exemplary transverse connector 100 for interconnecting a pair of longitudinal members or rods (not shown in the figure) that can be connected to vertebrae of a spinal column. It is contemplated that the transverse connector 100 can interconnect any suitable longitudinal member, such as plates or rods of other shapes, such as hexagonal rods. The rods can be located anywhere along the spinal column. In one embodiment the longitudinal spinal rods are on either side of the mid-sagittal plane of the spine. Each of the rods can be elongate and have sufficient length to span at least two vertebrae. A plurality of fixation elements can connect the rods to the vertebrae. The fixation elements can be of any known or desired configuration. In an embodiment, the fixation elements are pedicle screw assemblies that include a receiver member that removably mates with a screw member in a poly-axial or mono-axial configuration.

At least one transverse connector 100 can interconnect rods across the vertebral midline. The transverse connector 100 blocks relative movement of the rods so that the vertebrae connected to the rods are maintained in their desired relative positions and do not pivot relative to an anterior/posterior axis or a longitudinal central axis of the spinal column, or vertebral midline. The transverse connector 100 increases the torsional strength of the rod construct to provide stability when the spinal column twists, such as when the shoulders are turned or angled relative to the legs in a standing position. The transverse connector 100 can be located anywhere along the rods and any number of transverse connectors 100 can be used.

Figure 2:
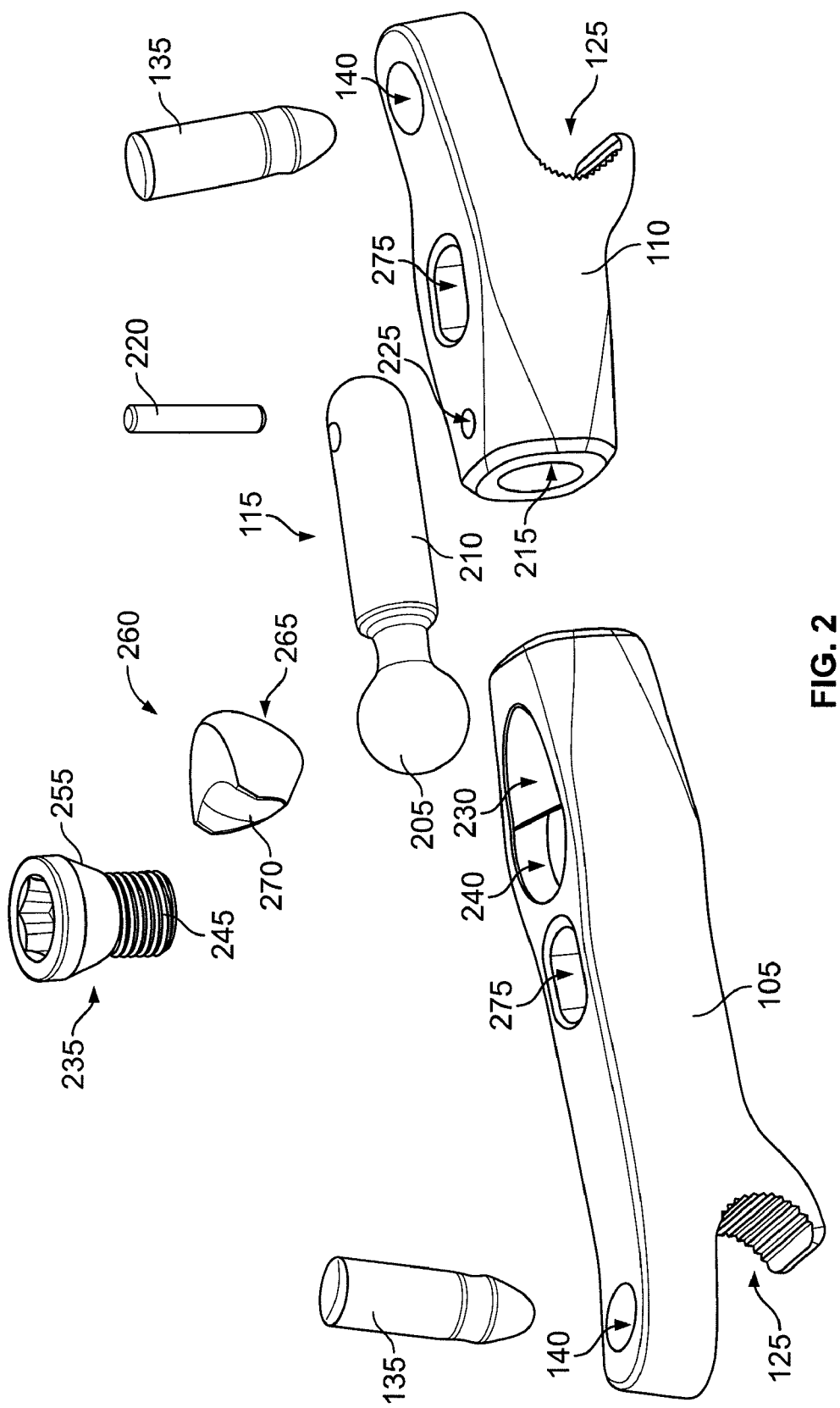
FIG. 2 shows an exploded view of the transverse connector assembly embodiment of FIG. 1.

With reference to FIGS. 1 and 2, the transverse connector 100 includes longitudinal rod engagement elements or connecting arms. A first connecting arm 105 and a second connecting arm 110 extend toward each other between each longitudinal member or spinal rod. The first and second connecting arms 105, 110 can connect by a variety of mechanisms or configurations. The first and second connecting arms 105, 110 can be generally elongate and positioned a distance apart from one another. The first and second connecting arms 105, 110 can be adjusted transversely. The first and second connecting arms 105, 110 can also be angularly and rotationally adjusted relative to one another to allow the connecting arms 105, 110 to be positioned as desired. The transverse, angular and rotational adjustability of the transverse arms 105, 110 with respect to one another allows them to mate to parallel, non-parallel, diverging, and converging spinal rods that are implanted within a patient's spinal system.

One embodiment of a transverse connector assembly 100 includes a first connecting arm 105 and a second connecting arm 110. The connecting arms 105, 110 mechanically link or connect to each other transversely (i.e., across the midline of the vertebral column) in a male-female relationship to be described in more detail below. For example, the connection can be by way of an intermediate element 115 that forms a central joint 120 with connecting arm 105. The joint 120 permits relative articulation of the arms 105, 110 and allows for transverse as well as angular and rotational adjustability of the transverse connector 100, also to be described in more detail below. The joint 120 is adapted to be selectively locked in order to fix the desired angle of connection between the connecting arms 105, 110 along a spinal column of a patient.

The connecting arms 105, 110 are elongated structures that contact rods near their lateral ends at rod engagement portion 125. The rod engagement portion 125 has a generally vaulted geometry that mates with the external surface of the connecting rods. The rod engagement portion 125 can have a splined or knurled mating surface 130. The knurled mating surface 130 reduces rotational instability associated with the engaging surfaces of the hinged transverse connector 100 and the connecting rods. Similarly, the connecting rods can have a splined or knurled surface that further enhances contact between the mating surfaces to reduce rotational instability.

A person skilled in the art will appreciate that while the transverse connector 100 is described herein as being adapted to engage a spinal fixation element, such as a spinal fixation rod, that a transverse connector disclosed herein can be configured to engage a variety of spinal fixation devices, such as anchors, cables, fixation plates, etc. For simplicity, the fixation element engaged by the transverse connector will be described herein as a longitudinal rod. Moreover, the transverse connector 100 can include only one connector member for engaging a spinal fixation device, and the opposed terminal end of the transverse connector 100 can be adapted for other uses. For example, the opposed terminal end of the transverse connector 100 can be configured to be fixedly attached to a vertebra. The transverse connector 100 disclosed herein can also include any combination of features described and/or illustrated herein, and the transverse connector 100 is not limited to the illustrated embodiment.

Figure 5:
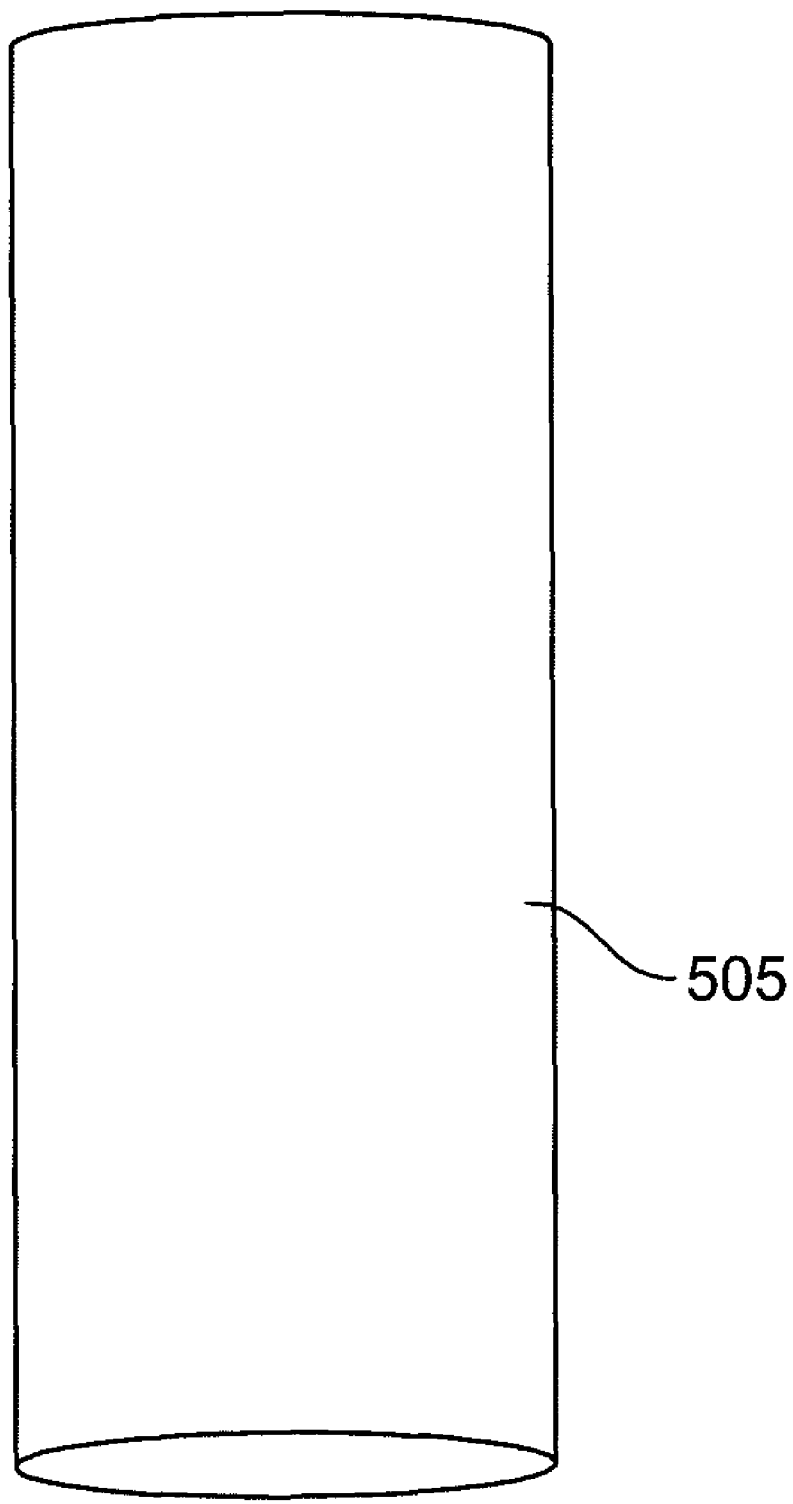
FIG. 5 shows a perspective view of an embodiment of a sleeve.

With reference to FIGS. 1 and 2, the connecting rods are held tight against the knurled mating surface 130 by a rod interference pin 135. The rod interference pins 135 (see FIG. 2) can be inserted through bores 140 extending through each of the connecting arms 105, 110 near the rod engagement portion 125. The interference pins 135 can be advanced into the bores 140 without a threaded interface. When the interference pins 135 are deployed through the bores 140 they are driven toward the connecting rod displacing it medially or toward the midline of the connector 100. The result is fixation of the rod against the mating surface 130 within the rod engagement portion 125 by an interference fit. The vaulted region of the rod engagement portion 125 can be associated with some elastic deformation such that a tighter interference fit is achieved. The interference pin 135 can be of any number of shapes to effect an interference fit with the rod engagement portion 125 of the connecting arms 105, 110. For example, the interference pin 135 can have a tapered or generally conical shape. In one embodiment, the interference pin 135 has an "hour-glass" profile such that the convex outer wall of the rod rests within the concavity or "waist" of the interference pin 135 when in the secured or locked position. The interference pins 135 can also be sheathed with a sleeve 505 or the like in order to accommodate longitudinal rods of varying diameters (see FIG. 5). The interference pins 135 can also have shapes that provide for insertion through and removal from the bore 140 such as with a tool adapted for such procedures.

As mentioned above, the connecting arms 105, 110 connect to each other transversely across the midline of the vertebral column by way of an intermediate element 115 that connects to and forms a medial joint 120 with connecting arm 105 permitting relative articulation. This articulating mechanical linkage between the arms 105, 110 involves at least two mating surfaces each having segments of contacting spherical geometries capable of relative movement. The joint 120 can be a universal joint such as a ball and socket joint. A universal joint 120 allows for maximum angular and rotational as well as transverse adjustability of the connector 100. Such adjustability is particularly important in the connection of diverging and converging longitudinal rods. The joint can also be a hinge joint or other type of connection.

FIG. 2 shows the intermediate element 115 has an angularly and rotationally adjustable feature at one end, such as a ball or other spheroid member 205, and a stem region or elongate shaft 210 at the other end. The spheroid member 205 connects the intermediate element 115 to connecting arm 105. The elongate shaft 210 affixes the intermediate element 115 to connecting arm 110. The elongate shaft 210 is slidably inserted into an internal shaft or pocket 215 at the medial end of connecting arm 110 and is permanently affixed within the pocket 215 by way of locking pins 220 or other locking means. The locking pins 220 extend through bore 225 near the medial region of connecting arm 110.

The elongate shaft 210 can be of varying lengths. The different lengths provide for transverse adjustability of the transverse connector 100. The spheroid member 205 also provides some degree of transverse adjustability. For example, the spheroid member 205 can be positioned in such a way as to impart an A-frame architecture to the connector 100 and change the distance that the connector 100 can span. A further advantage of the A-frame architecture is that it allows for the connector 100 to avoid contact with the dura and/or the spinal column while in use. In addition, the connector 100 can have incorporated a protective stop that inhibits the A-frame architecture from collapsing past a pre-determined angle such that the connector 100 does not impinge on the dura. If the pre-determined maximum angle results in a transverse span of the connector 100 that is too short to clamp onto the elongate rods, the user can select a connector 100 having a different length shaft 210. The spheroid member 205 also provides angular and rotational adjustability to the connection between the intermediate element 115 and the connecting arm 105, to be described in more detail below.

Figure 3A:
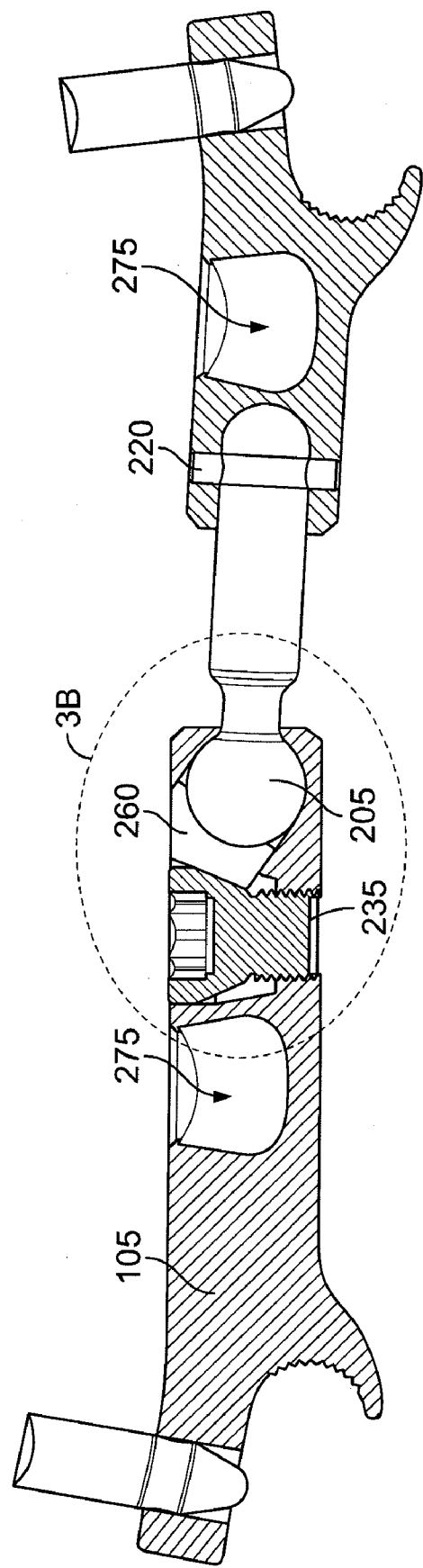
FIG. 3A shows a side, cross-section view of the transverse connector assembly embodiment of FIG. 1.
Figure 3B:
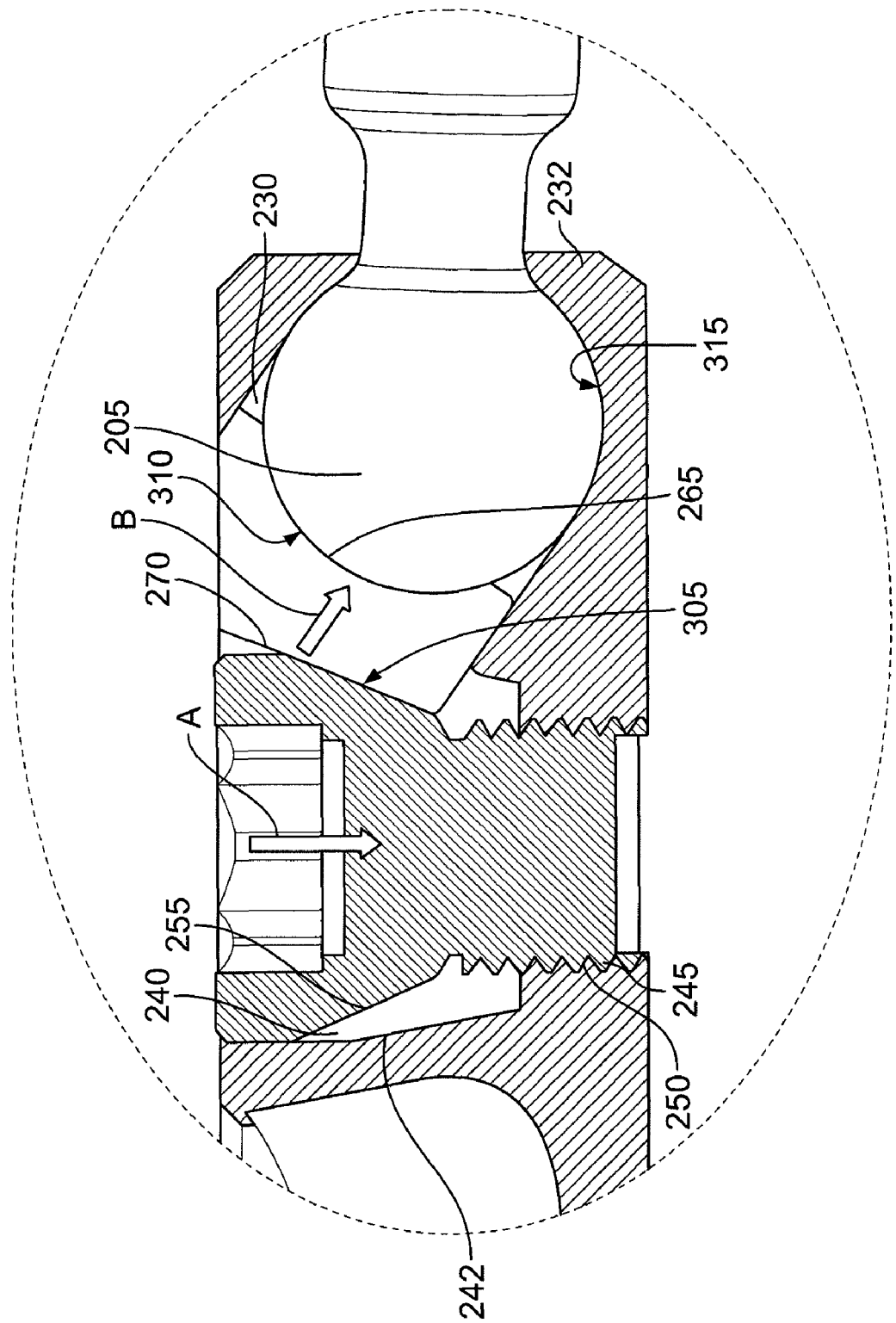
FIG. 3B shows a detail view at circle B of the transverse connector assembly embodiment of FIG. 3A.

The spheroid member 205 lies within bore 230 of connecting arm 105. FIGS. 3A and 3B illustrate how bore 230 extends from the upper surface of connecting arm 105 to the medial end of connecting arm 105 at an angle with respect to the longitudinal axis of the connecting arm 105. The internal surface of bore 230 near its medial opening has a shape that is at least partially spherical. The spherical portion of the bore's internal surface also forms a lip 232 near the medial opening such that the diameter of the medial opening of the bore 230 is smaller than the spheroid member 205. This prevents the spheroid member 205 from being pulled through the medial opening of the bore 230.

The spheroid member 205 and bore 230 along with a wedge member 260 form the joint 120 between the connecting arms 105, 110. The wedge 260 lies within bore 230 such that one end of the wedge 260 contacts the spheroid member 205. The end of the wedge 260 that contacts the spheroid member 205 forms a mating surface or socket 265 in which the spheroid member 205 can freely move. The socket 265 of the wedge 260 has a shape that mirrors the exterior surface of the spheroid member 205.

The rotational and angular position of the joint 120, such as after deployment of the connector 100 onto rods (to be described below), and thus the position of the connecting arms 105, 110 with respect to one another is fixed by an interference element such as a set screw 235 threaded through a bore 240 in connector arm 105. The set screw 235 displaces at least one mating surface and inhibits relative movement by displacing spherical surfaces against the other. As best shown in FIGS. 3A and 3B, bore 240 extends perpendicularly through connecting arm 105 and is accessible from the upper surface of the connecting arm 105. The internal surface of bore 240 has a tapered portion 242 and a threaded portion 250. The tapered portion 242 of bore 240 intersects bore 230 near the upper surface of the connecting arm 105 such that the openings of bores 230 and 240 unite into a single elongated opening at the upper surface of the connecting arm 105 (best shown in FIG. 2).

As described above, bore 230 receives wedge member 260. Bore 240 receives the set screw 235. One end of the wedge 260 has a mating surface 265 that contacts the spheroid member 205. The opposite end of the wedge 260 has a mating surface 270 that contacts the set screw 235. In particular, the mating surface 270 engages the tapered head 255 of the set screw 235 upon tightening of the set screw 235 into bore 240.

The set screw 235 has external threads 245 and the surface of the bore 240 has internal threads 250. Thus, rotation of the set screw 235, such as with a hex wrench, results in the set screw threads 245 engaging the bore internal threads 250 and tightening of the set screw 240 in a downward direction. As best shown in FIG. 3B, tightening of the set screw 235 in the downward direction (arrow A), results in the engagement of the tapered head 255 with mating surface 270 of the wedge member 260 (set screw/wedge interface 305). The tapered head 255 is such that the diameter increases as the set screw is further advanced in a downward direction (arrow A). This engagement results in the wedge 260 moving toward the spheroid member 205 (arrow B) and engagement of the mating surface 265 onto the spheroid member 205 (spheroid member/wedge interface 310). The wedge member 260 presses the spheroid member 205 against the lip 232 of the bore 230 (spheroid member/lip interface 315). In turn, the intermediate member 115 and the angular position of the connecting arms 105, 110 with respect to one another is fixed in place. It should be appreciated that all these mating surfaces can be textured to improve contact.

Figure 4A:
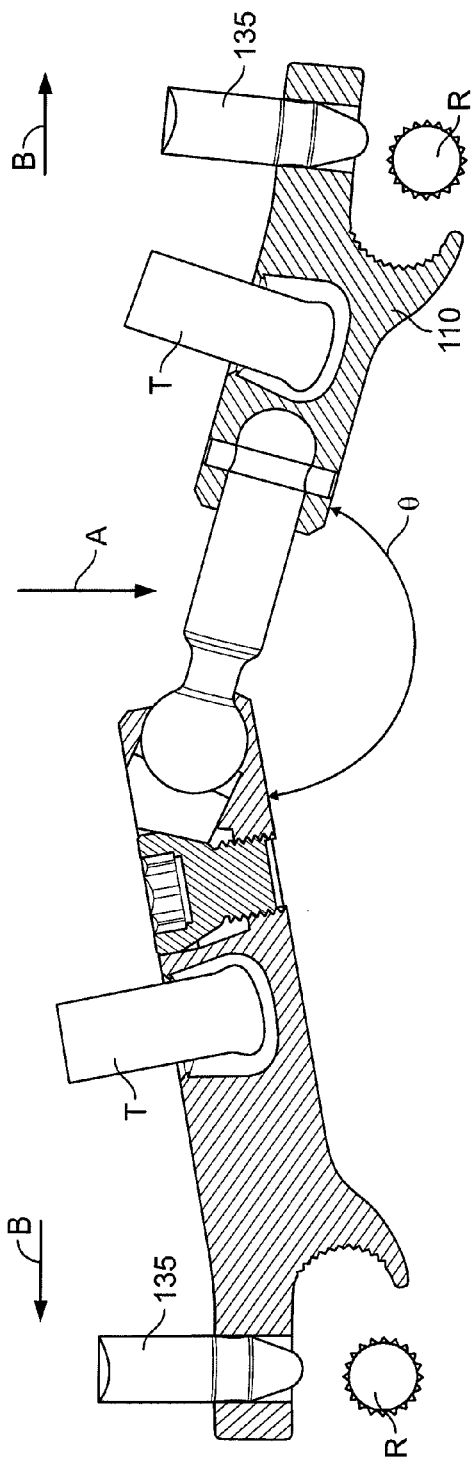
FIGS. 4A-4B show a side view schematic of placement of the transverse connector of FIG. 1 onto rods.
Figure 4B:
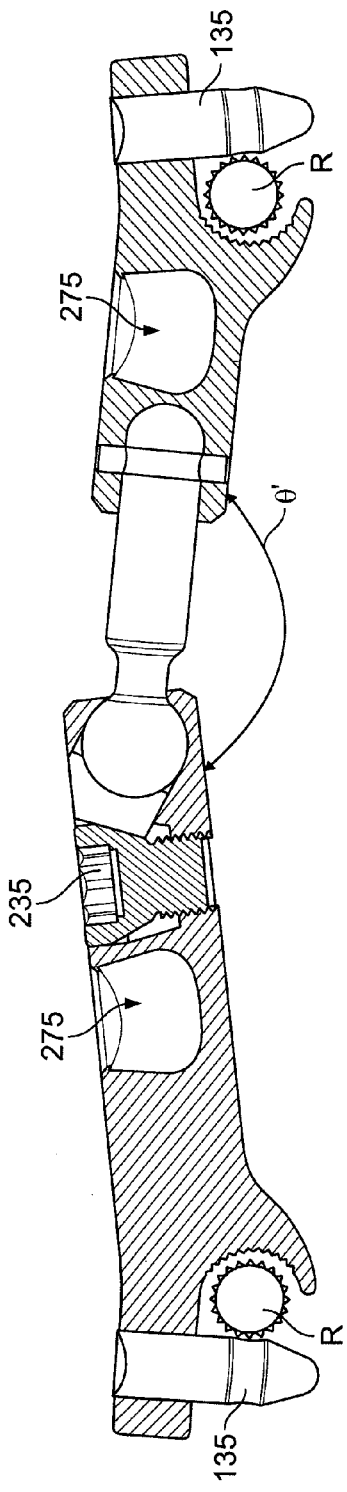

FIGS. 4A-4B show a side view schematic of placement of the transverse connector 100 onto rods R. Deployment of the connector 100 onto rods R can be performed, for example, by a tool such as a hinged deployment tool having contacting elements T. An operator can place the tool contacting elements T into recesses or pockets 275 open to the upper surface of each connecting arm 105, 110. The tool contacting element T can have a shape that is generally spherical to help engage the internal pocket 275 surfaces, which can be in non-parallel planes. Relative articulation of the two connecting arms result from separation or approximation of the tool contacting elements T For example, separating the tool contacting elements T causes the joint 120 to straighten or the A-frame to collapse and move in a generally downward direction (Arrow A). Simultaneously, the connecting arms 105, 110 move in a generally lateral or outward direction (Arrows B). The rods R are forced into the rod engagement portions 125 of each of the connecting arms 105, 110. Further, angle θ (FIG. 4A) of the A-frame architecture of the connector 100 increases, for example, to angle $\theta^1$ (FIG. 4B) as the A-frame further collapses. Upon placement of the connector 100 onto the rods R, the set screw 235 can be tightened as described above to fix the position of the connector 100. Similarly, interference pins 135 can be deployed such that they form an interference fit with the rods R and the vaulted region of the rod engagement portions 125.

As described above, the connector 100 can have incorporated a protective stop that inhibits the angle of the A-frame architecture from exceeding a pre-determined angle such that the connector 100 does not impinge on the dura. If the pre-determined maximum angle results in a transverse span of the connector 100 that is too short to clamp onto the elongate rods, the user can select a connector 100 having a different length shaft 210.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Only a few examples and implementations are disclosed. Variations, modifications and enhancements to the described examples and implementations and other implementations may be made based on what is disclosed.

What is claimed is:

1. A spinal transconnector device for coupling longitudinal spinal rods on either side of the mid-sagittal plane, comprising:
   a first rod engagement element, comprising a convex spherical element; and
   a second rod engagement element, comprising:
   a passage for receiving the convex spherical element, at least a portion of the passage having a first concave spherical surface geometry that can mate with at least a portion of the convex spherical element;
   a first interference element comprising a second concave spherical surface geometry, wherein the convex spherical element articulates within the passage and is sandwiched between the first concave spherical surface of the passage and the second concave spherical surface of the first interference element; and
   a second interference element having a segment of its surface in the form of a truncated cone, wherein advancement of the second interference element into a bore in the second rod engagement element approximates the second concave spherical surface toward the first concave spherical surface.

2. The device of claim 1, wherein approximation of the first and second concave spherical surfaces to each other substantially inhibits relative movement between the convex spherical element and the first and second concave spherical surfaces.

3. A device as in claim 1, wherein the second interference element has a threaded region.

4. A device as in claim 1, wherein the diameter of the second interference element increases with its advancement in the bore.

5. A device as in claim 1, wherein at least one of the first concave spherical surface of the passage, the second concave spherical surface of the first interference element, the convex spherical element or the second interference element is textured.

6. A spinal transverse connector device for coupling spinal rods, comprising:
   a first longitudinal element comprising a passage and a threaded bore, wherein a portion of the passage intersects a portion of the threaded bore;
   a second longitudinal element comprising a bore;
   a connector element connecting the first and second longitudinal elements, the connector element comprising a convex spherical region and a stem region, wherein the convex spherical region extends into the passage of the first longitudinal element and the stem region extends into the bore of the second longitudinal element, and wherein the convex spherical region has a diameter that exceeds a diameter of an opening into the passage, the opening surrounded by internal walls having partially spherical concave surface geometry;

a first interference element comprising a first surface that has a generally concave conical geometry and a second surface that has a generally concave spherical geometry; and a second interference element comprising a first region that has a convex truncated conical surface geometry and a second region that has a threaded surface geometry, wherein advancement of the second interference element into the threaded bore presses the first region of the second interference element against the first surface of the first interference element displacing the first interference element towards the convex spherical region of the connector element thereby pressing the convex spherical region against the internal walls surrounding the passage opening therein forming three generally spherical mating surfaces whose approximation to each other inhibits relative movement between the first and second longitudinal elements.

7. A device as in claim 6, wherein the diameter of the second interference element increases with its advancement into the threaded bore.

8. A device as in claim 6, wherein at least one of the three generally spherical mating surfaces is textured.

* * * * *